United States Patent [19]

Komiyama

[11] Patent Number: 4,774,129

[45] Date of Patent: Sep. 27, 1988

[54] GAS-SENSITIVE COMPOSITE MATERIAL COMPRISING METAL AND DIELECTRIC

[75] Inventor: Hiroshi Komiyama, Tokyo, Japan

[73] Assignee: Toa Nenryo Kogyo K.K., Tokyo, Japan

[21] Appl. No.: 942,037

[22] Filed: Dec. 15, 1986

Related U.S. Application Data

[63] Continuation of Ser. No. 780,478, Sep. 26, 1985, abandoned.

[30] Foreign Application Priority Data

Sep. 29, 1984 [JP] Japan .............................. 59-203016

[51] Int. Cl.⁴ .................. B32B 3/26; B32B 5/14; B32B 5/22; B32B 7/00
[52] U.S. Cl. .......................... 428/213; 428/307.7; 428/312.6; 428/312.8; 428/315.7; 428/317.9; 428/433; 428/472
[58] Field of Search .................. 427/101; 428/304.4, 428/315.5, 315.7, 315.9, 317.9, 319.1, 213, 215, 307.7, 312.6, 312.8, 433, 469, 472

[56] References Cited

U.S. PATENT DOCUMENTS

| | | | |
|---|---|---|---|
| 4,082,863 | 4/1978 | Dancy et al. | 427/181 |
| 4,225,634 | 9/1980 | Tanaka et al. | 427/101 |
| 4,281,041 | 7/1981 | Koehler | 428/336 |
| 4,481,234 | 11/1984 | Kolpe et al. | 427/71 |
| 4,592,967 | 6/1986 | Komatsu et al. | 428/697 |
| 4,654,228 | 3/1987 | Komiyama | 427/180 |

OTHER PUBLICATIONS

W. D. Kingery, et al. Introduction To Ceramics, 2nd Edition, John Wiley & Sons, New York, N.Y. (1976), pp. 847, 850-853, 862-863, 882-885, 904-907, 912-913 and 954-955.

*Primary Examiner*—William J. Van Balen
*Attorney, Agent, or Firm*—Seidel, Gonda, Goldhammer & Abbott

[57] ABSTRACT

A gas-sensitive composite material comprises a porous dielectric having micropores and a thin film consisting of ultrafine metal particles dispersed in, and supported by, at least the porous surface layers of the dielectric.

The gas-sensitive composite material is produced by a method comprising the steps of: forming a thin film of conductive ultrafine metal particles on at least the porous surface layers of a porous dielectric and dispersing the thin film metal, in a size similar to the pore opening, continuously or partly discontinuously in the porous layers, whereby a three-dimensional composite material is obtained.

7 Claims, 7 Drawing Sheets

○ Silver particles
— Electrical connections among particles

GAS-SENSITIVE COMPOSITE MATERIAL COMPRISING METAL AND DIELECTRIC

This is a continuation of co-pending application Ser. No. 780,478, filed on Sept. 26, 1985, abandoned.

FIELD OF THE INVENTION

This invention relates to a gas-sensitive composite material comprising a metal and a dielectric and also to a process for producing the same. More particularly, the invention concerns a gas-sensitive composite material comprising a metal and a dielectric and which has switching and memory effects and a process for producing the same.

DESCRIPTION OF THE PRIOR ART

It is well-known that metals undergo significant changes in their electrical properties when they are formed into thin films. FIG. 14 is a graph showing the relation between the surface resistance of a deposited film of gold having a mass film thickness of 10 to 100 Å and the film thickness and also the relation between the surface resistance and temperature where the film thickness is kept constant. The graph indicates that a thin film having a film thickness of less than about 70 Å is discontinuous and the resistance is remarkably high, with the temperature dependence of the resistance similar to that of a semiconductor.

Thus, conductive thin films are known to vary widely in their properties depending on whether they are continuous or discontinuous. The continuous film having a thickness about equal to or less than the mean free pass of electrons (approximately several hundred angstroms at ordinary temperatures) produces a size effect whereby a considerable influence is exerted on the transport of electrons by the two parallel planes. Structural defects that can originate from the process of film formation tend to cause scatter of electrons. These result in the notable phenomenon that the specific resistance of a thin film generally is greater than that of a bulk. Discontinuous thin films, on the other hand, vary greatly in structure according to the forming conditions used. Therefore, their properties have only qualitatively been grasped. The known properties common to them are (1) very high resistance,
(2) thermoactive temperature dependence of the resistance or conduction,
(3) non-Ohmic nature,
(4) reversible-irreversible changes due to gas adsorption, and
(5) much current noise and frequent exhibition of 1/f characteristic.

Discussions on electrical conduction through discontinuous thin metal films have been made known by "Thin Solid Films", vol. 47, pp. 3-65. Theories proposed in the past as to electrical conduction are
(a) thermionic emission model,
(b) activated tunneling model using small insular charge energy as the activation energy, and
(c) tunneling model by the use of substrate impurities and surface state.

These theories are all based on simple electrical conduction between two islands. Thus, when an insular thin film is exposed to ordinary environments it exhibits a high negative temperature coefficient of resistance (TCR) and becomes instable. For these reasons the discontinuous thin metal films have not been in practical use. Some other potential uses have been suggested for the discontinuous films which might have found practical applications only if the stability problem were overcome. They are electrical applications including biomedical instruments such as high-sensitivity strain gages, deviation gages, temperature sensors, infrared (IR) detectors, gas detectors, nonlinear registers, electronic or optical emitters, and high-resolution vidicon electrodes. Other applications in non-electronic fields have also been proposed, such as the use of insular permalloy films that attain enhanced hysteresis effects, utilization of the light absorptivity of the films in solar heat collectors, and development of position sensors.

As described above, discontinuous thin metal films have not lent themselves easily to practical use because of wide variation in structure with the forming conditions, structural instability under ordinary service conditions as in air, and high negative temperature coefficient.

It is accordingly an object of the present invention to provide a composite material with gas sensitivity comprising a metal and a dielectric as defined in the appended claims and capable of allowing the above-mentioned thin metal film to display its characteristics quantitatively.

Another object of the present invention is to provide a process for producing a composite material with gas sensitivity of the type described.

SUMMARY OF THE INVENTION

Briefly, the present invention provides a gas-sensitive composite material comprising a porous dielectric having micropores and a thin film consisting of ultrafine metal particles dispersed in, and supported by, at least the porous surface layers of the dielectric.

In another aspect, the present invention provides a process for producing a gas-sensitive composite material comprising a metal and a dielectric characterized by forming a thin film of conductive ultrafine metal particles on at least the porous surface layers of a porous dielectric and dispersing the thin film metal, in a size similar to the pore opening, continuously or partly discontinuously in the porous layers, whereby a three-dimensional composite material is obtained.

BRIEF DESCRIPTION OF THE DRAWINGS

These and other objects and features of the present invention will be fully understood from the following detailed description of the invention taken with reference to the accompanying drawings, in which.

DETAILED DESCRIPTION OF THE PREFERRED EMBODIMENTS

Figure 1:
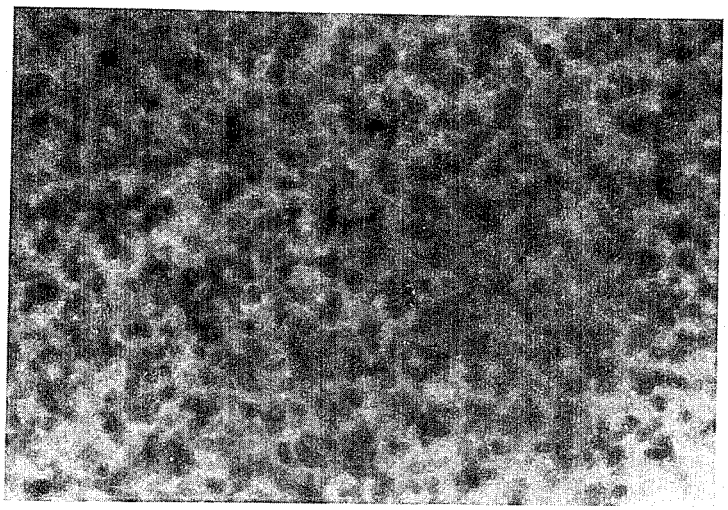
FIG. 1 is a transmission electron micrograph of the surface layer configuration of a gas-sensitive composite material comprising a metal and a dielectric according to the invention.

Heretofore, semiconductors have been employed as gas sensors since their electrical conductivities change with gas adsorption on the surface. For example, gas sensors using a sintered n-type semiconductor consisting chiefly of $SnO_2$ and stabilized-zirconia gas sensors that make use of the electrochemical potential difference between the two sides of the film are known in the art.

Discontinuous thin metal films possess electrical properties like those of semiconductors, since electrons are moved among metal particles by a quantum-mechanical tunneling effect as noted above. They therefore appear to have a possibility as gas sensors. However, the instability of the discontinuous thin films themselves has hindered their adoption as practical sensors, and their gas-sensing properties have not been known either.

It has now been found that such an instable, discontinuous thin film of a metal can be stabilized when it is dispersed in, and supported by, at least the porous surface layers of a dielectric base having micropores. Electric responses of the resulting element with respect to $O_2$, $C_2H_4$, $H_2$, and/or $N_2$ were investigated. It has then been found that the element performs switching and memory functions. These findings have led to the perfection of the present invention.

The present invention will now be described in detail.

The gas-sensitive composite material according to the invention is one comprising a metal and a dielectric characterized by a porous dielectric material having micropores and a thin film composed of ultrafine metal particles dispersed in, and supported by, at least the porous surface layers of the dielectric base.

As the dielectric substance, at least one chosen from metal oxides and metal nitrides having dielectric properties may be employed. Specifically, at least one oxide or nitride of a metal selected from the metals of Groups IIA, IIIA, IIIB excluding boron, IVB excluding carbon, VA, VIA, and VIB excluding oxygen and sulfur in the Periodic Table may be used. Among these, porous glass, $TiO_2$-containing porous glass, porous alumina, porous titania, porous zirconia and the like are preferred because they are relatively easy to fabricate.

It is beneficial for the sake of gas sensitivity that the element have micropores 500 Å or smaller in size in a total volume accounting for 10 to 70% of the total volume of at least the porous surface layers of the porous dielectric substance. Also, the porous surface layers desirably have a thickness in the range of 50 to $10^7$ Å each.

The thin film of ultrafine metal particles may consist of ultrafine particles of at least one metal selected from Ag, Au, Cu, Fe, Co, Ni, Ru, Rh, Pd, Pt, Ir, Cr, Al, Zn, Sn, In, and Pb.

The gas-sensitive composite material of the invention is sensitive to $O_2$, $N_2O$, $NO_2$, $SO_2$, $SO_3$, CO, $H_2$, $NH_3$, methane, ethylene, ethane, propylene, propane, $SiH_4$, $AsH_3$, $BH_3$, metal alcoholates, trimethylaluminum and the like. For example, Group VIII elements are known to have specific adsorptive actions upon CO, NO, $H_2$, etc., Cu, Fe and the like upon $NH_3$, and Pt and Pd upon $SO_2$, and therefore they are effective as selective sensors.

Then, the composite material of the invention will be described below in connection with examples of experiments conducted therewith.

A substrate piece of glass marketed by Corning Glass Works of the U.S. under the trade designation "Vycor glass #7930" which has a mean pore opening of 40 Å (each piece measuring 1 cm long, 0.5 cm wide, and 0.1 cm thick) was impregnated with a 2N aqueous solution of silver nitrate-ammonia complex salt and dried. The cycle of impregnation and drying was repeated until the silver content of the complex salt in the substrate reached a predetermined value. The substrate was then dipped in 35 wt % aqueous formaldehyde to reduce the complex salt to metallic silver.

Referring to FIG. 1, which is a transmission electron micrograph, black spots represent silver dispersed continuously or partly discontinuously in a porous glass which looks white, in sizes similar to the pore openings of the substrate. The micrograph shows the silver and the substrate combining in the form of a three-dimensional composite material. In contrast with the conventional thin metal films described above that are two-dimensional island-group aggregates, the composite material of FIG. 1 takes the form of a three-dimensional composite (congromerate).

Figure 2:
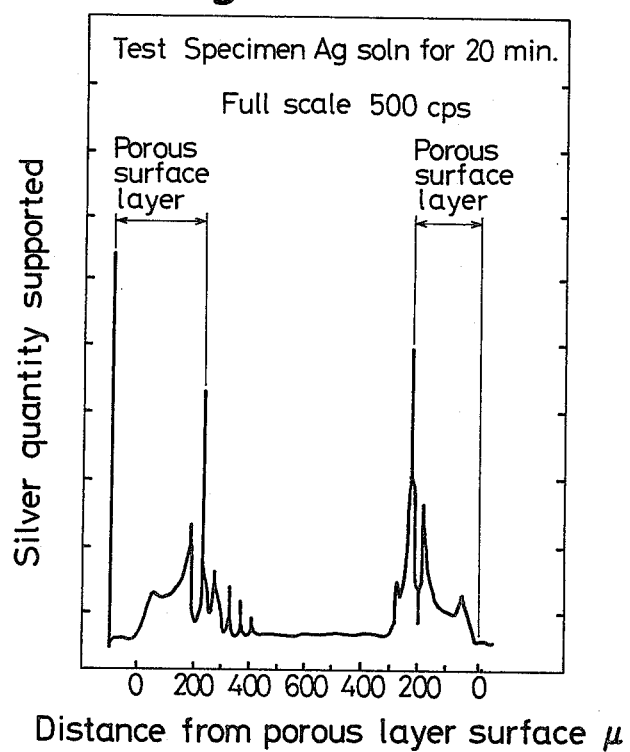
FIG. 2 is a graphic representation of distances from the both side surfaces of a porous composite material of the invention after immersion in an aqueous silver nitrate solution for 20 minutes to the inside layer thereof and the quantities of silver supported by the substrate portions at the respective distances.
Figure 3:
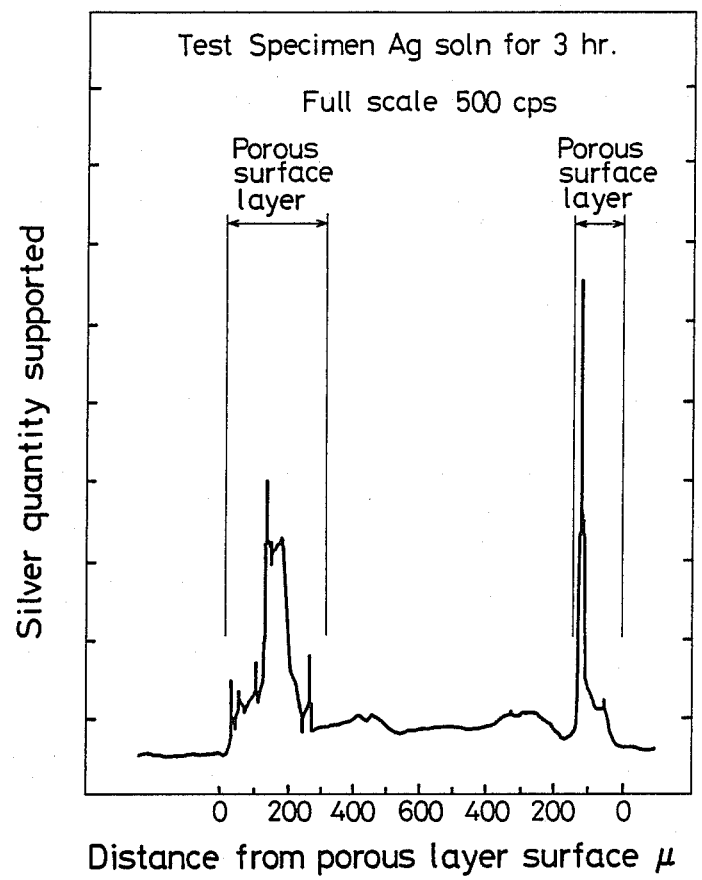
FIG. 3 is a graph showing the relation between the distances from the surfaces to the inside layer of a porous composite material after immersion in an aqueous silver nitrate solution for 3 hours in accordance with the invention and the quantities of silver supported at the respective distances.

FIG. 2 is a graphic representation of distances (in $\mu m$) from the porous substrate surfaces to the inside layer and the quantities of silver supported by the substrate portions at the respective distances, as determined by EPMA. For this test the porous glass substrate explained above was immersed in a 2N aqueous solution of silver nitrate-ammonia complex salt for 20 minutes, dried, and then dipped in the above-mentioned aqueous formaldehyde to have the silver deposited in, and supported by, the pores of the substrate. FIG. 3 is a graph showing the distances (in $\mu m$) from the surfaces to the inside layer of a substrate immersed in the aqueous complex salt for 3 hours and from then on treated in the same manner as with the substrate of FIG. 2 versus the quantities of supported silver measured at the respective distances. The two graphs indicate that silver is supported practically by only the both surface layers of the substrate. Nevertheless, this structure has been found to function adequately as a gas-sensitive composite material of the invention, as will be described later.

Figure 4:
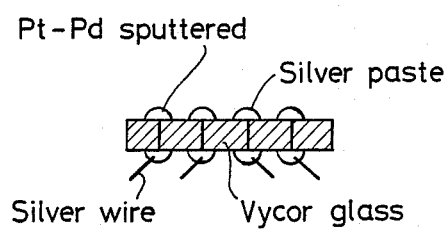
FIG. 4 is a side view of an element according to the invention, with electrodes fitted in place.
Figure 5:
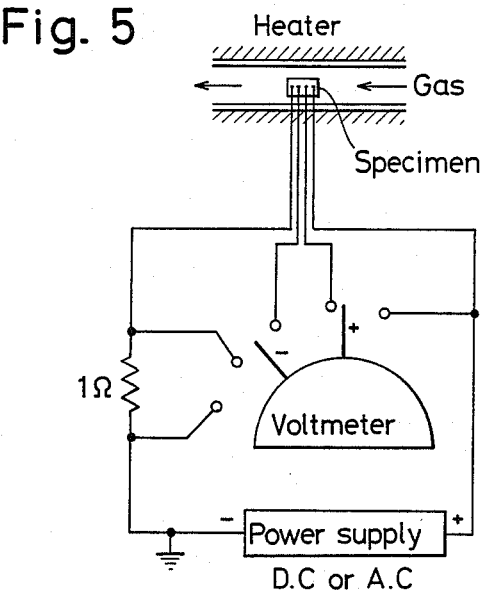
FIG. 5 is a schematic view of a measuring instrument having an electric circuit for measuring changes in electrical properties upon gas detection of the element of the invention placed in a gas stream.

Next, the both sides of the above composite material were polished with sandpaper and, as shown in FIG. 4, a Pt-Pd alloy was deposited by sputtering on symmetric points on opposite sides. Copper wire was wound transversely round the composite to bind each pair of the sputtered points together with the substrate, and the sputtered points were covered with silver paste. The composite material was then fired at 300° C. The fired composite element thus obtained (hereinafter called "element") was, as shown in FIG. 5, held in a glass tube 2 cm in diameter and connected to instruments for the measurement of its electrical properties. Oxygen, ethylene, hydrogen, and/or nitrogen gas was passed through this glass tube at a flow rate of 200 cm$^3$/min and at the atmospheric pressure. At the same time, the element was heated from the outside of the glass tube to 300° C. and was connected to an electric circuit to determine its electrical conductivity.

Figure 6:
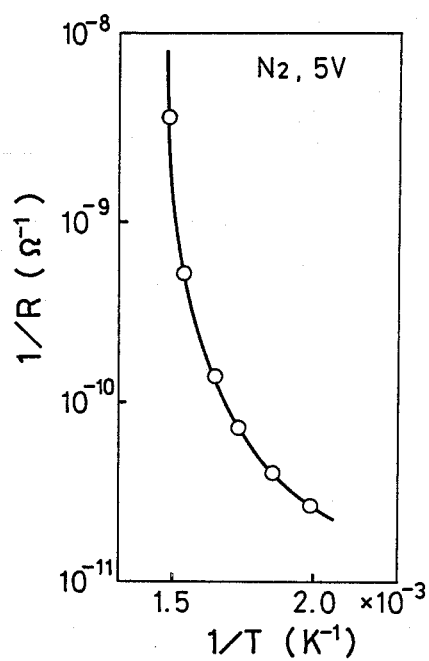
FIG. 6 is a graph showing the relation between the temperature (K) and resistance ($\Omega$) of the element of the invention in an $N_2$ gas stream as measured by the instrument of FIG. 5.

Before it was caused to support silver, the porous glass (Vycor glass) was tested for the temperature dependence of its electrical conductivity. The results are graphically represented in FIG. 6. The graph reveals that the activation energy varies depending on whether the temperature is high or low. This is presumably ascribed to the fact that at low temperatures the glass which is an insulator has a very low conduction electron density and the surface structural defect or the like becomes more contributory to the electrical conductivity.

Figure 7:
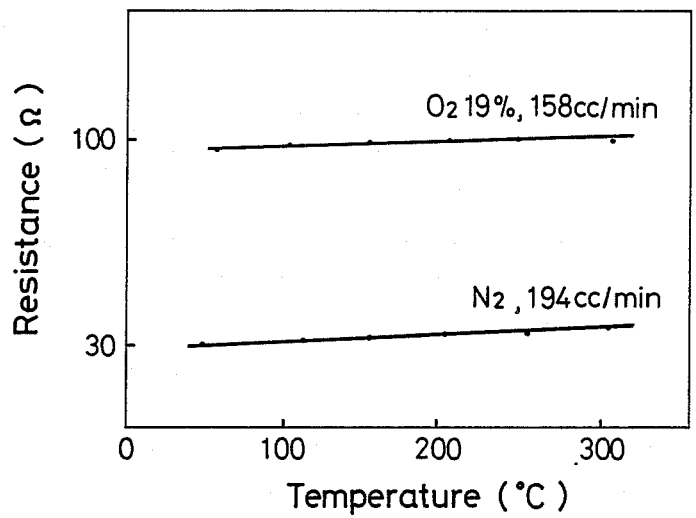
FIG. 7 is a graph showing the relations between the temperature (°C.) and resistance ($\Omega$) of the element of the invention placed in a gas stream of $N_2$ gas along or 19% $O_2$ and the balance $N_2$ as measured by the instrument of FIG. 5.

The temperature dependence of the electrical conductivity of the element fabricated as above in conformity with the invention was determined by placing test specimens of the element in two different gas streams of $N_2$ at a flow rate of 194 cc/min and of an $N_2$ gas stream containing 19% $O_2$ at 158 cc/min. FIG. 7 shows the results. The volume of silver supported by this element amounted to 40% of the volume of the porous surface layers. It can be seen from this graph that the temperature coefficient of resistance ($\Omega$) in the temperature range from ordinary temperature to 350° C. is low regardless of the kind of the gas constituting the stream. The graph indicates also that the resistance value with the oxygen-containing gas stream is about 3.3 times the value with the nitrogen gas stream. The low temperature coefficient makes the element very advantageous in practical applications over the conventional discontinuous films. From the foregoing phenomena it is obvious that the element of the invention does not possess the properties characteristic of either metals or semiconductors. However, because the temperature coefficient of resistance of a metal film is directly proportional to the specific resistance of the film, the element may be deemed similar in that one property to the known thin films.

Figure 8:
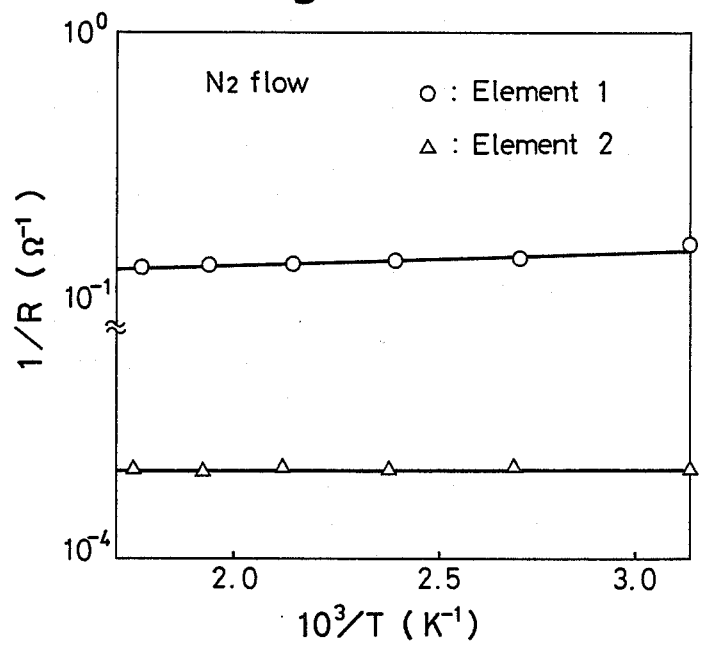
FIG. 8 is a graph showing the relations between the temperature (K) and resistance ($\Omega$) of Elements 1 and 2 in $N_2$ gas stream as measured by the instrument of FIG. 5.

The relations between the temperature and resistance in a nitrogen gas stream of two elements according to the invention, i.e., Elements 1 and 2 in which silver accounted for 40% and 15%, respectively, of the volume of the supporting porous surface layers, were examined. FIG. 8 graphically summarizes the results. The graph indicates that the element with a very low temperature coefficient of resistance and containing 15% silver exhibits a resistance higher than that of the 40% silver element by four orders of magnitude.

Figure 9:
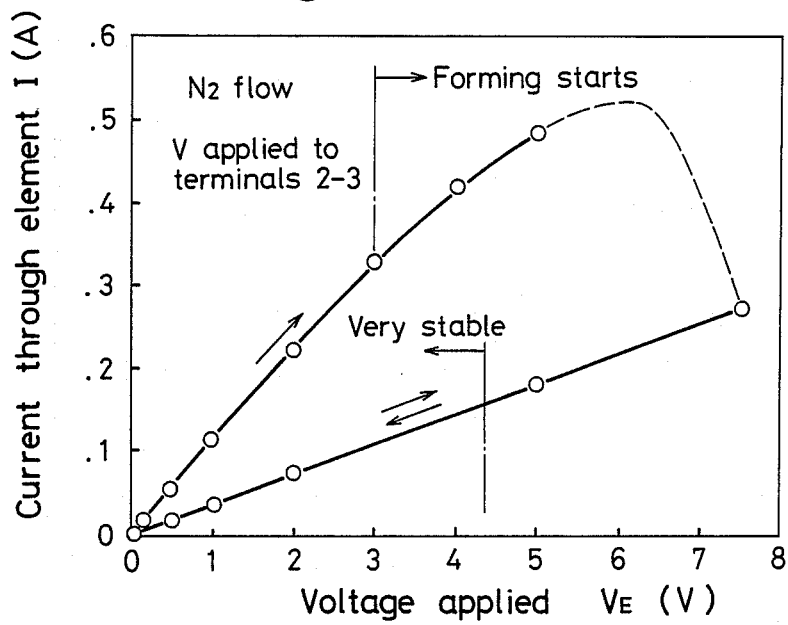
FIG. 9 is a graph showing the relation between the applied voltage $V_E$ (V) and the current I (A) in the element when the voltage was applied to terminals 2 and 3 of the element of the invention in an $N_2$ stream.

FIG. 9 shows the results of investigations made about the relationship, in a nitrogen stream, between the applied voltage and the current passing through specimens of an element according to the invention wherein silver supported by the porous surface layers accounted for 35% by volume of the latter. As the applied voltage was gradually increased, the resistance increased correspondingly, but beyond 3V the resistance rose sharply. After that, the applied voltage was decreased. With the voltage below 4V, the element attained stabilized resistance and became extremely stable upon repeated use. This phenomenon, already reported in the literature with regard to two-dimensional discontinuous films in high vacuum, is known as "forming". It follows that the element of the invention maintains stability of its resistance even at the atmospheric pressure, as long as it is used at voltages not exceeding the point where the forming begins to take place. The phenomenon presumably results from the stabilization of the contours and locations of silver particles by dint of Joule heat in a very limited portion of the element, for example, by the scission of filamentary links or connections and separation of silver particles into globules independent of one another.

Figure 10:
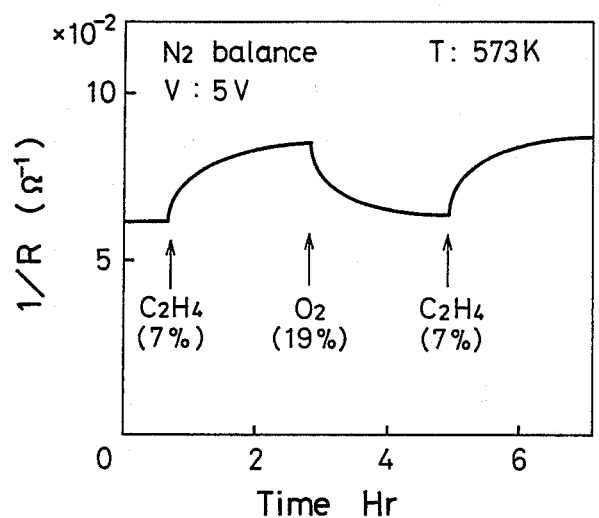
FIG. 10 is a graph showing the relations between the resistance ($\Omega$) and time measured by the instrument of FIG. 5 of the element of the invention before forming, by changing over the gas stream from 7% $C_2H_4$ and the balance $N_2$ to 19% $O_2$ and the balance $N_2$.

Next, an element of the invention prior to forming was placed in alternately flowing streams, one consisting of 7% $C_2H_4$ and the balance $N_2$ and the other consisting of 19% $O_2$ and the balance $N_2$, at a temperature of 573° K. and a voltage of 5V. The relation between the time (hr) and the current (mA) was as shown in FIG. 10. It is manifest from the graph, in which the value of current passing through the element varies with each change-over of the gas stream, that the element can serve as a gas sensor. It exhibits a high resistance in the oxygen-containing atmosphere and a low resistance in the ethylene-containing atmosphere. This phenomenon apparently stems from the fact that oxygen is a gas having a high electro-negativity.

Figure 11:
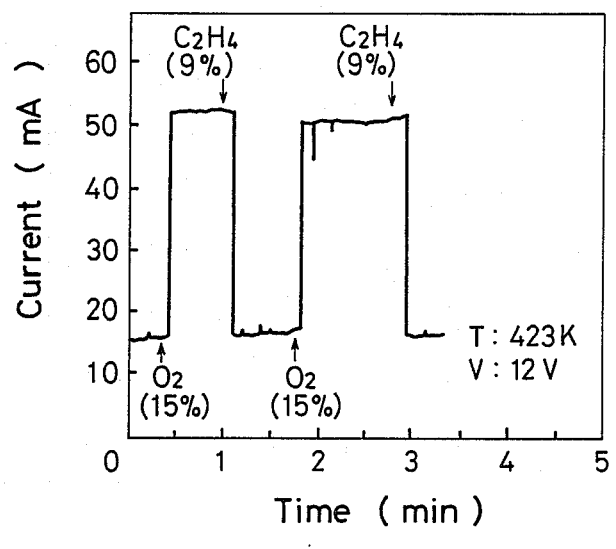
FIG. 11 is a graph showing the relations between the resistance ($\Omega$) and time measured by the instrument of FIG. 5 of the element of the invention after forming, by changing over the gas stream from 15% $O_2$ and the balance $N_2$ to 9% $C_2H_4$ and the balance $N_2$.

A similar test was conducted with an element of the invention after its forming, using alternating flow streams of nitrogen gases containing oxygen or ethylene in the same concentrations as in FIG. 10 but at a temperature of 473° K. FIG. 11 graphically summarizes the results. The test showed that the change in resistance with the change-over of the gas stream was instantaneous. The speed of response was as high as $10^{-5}$s and the element had a threshold voltage. This unusual phenomenon, as illustrated in FIG. 9 is hereinafter called "switching". In brief, it is characterized by the following:

(a) It exhibits a low resistance in an oxygen-containing gas and a high resistance in an ethylene-containing gas.

(b) In this case the relation between voltage (V) and current (mA) is as shown in FIG. 10, or linear (Ohmic).

(c) The speed of response to the gas change-over is extremely high.

(d) The response occurs at ordinary as well as other temperatures, and the response speed changes little with temperature.

(e) Once the applied voltage is decreased below the threshold, the element undergoes no more change in resistance regardless of change-over of the atmosphere. In other words, it has a "memory" effect.

(f) Switching is a reversible change and is repeatable. The function remains stable for long unless any excessive voltage is applied.

(g) The phenomenon takes place, with the same characteristics, in atmosphere containing a very low concentration; say 500 ppm, of $O_2$ or $C_2H_4$.

The unique behavior after forming of the element according to the invention, which is yet to be fully clarified, will now be briefly explained with reference to FIGS. 12 and 13.

Figure 12:
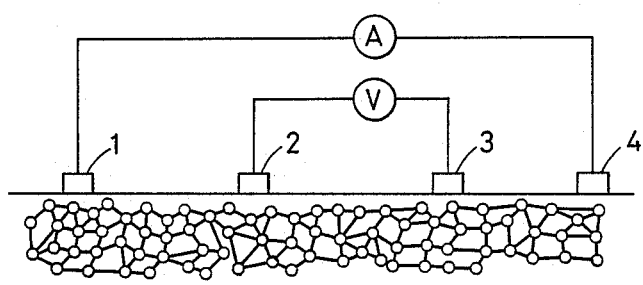
FIG. 12 is a schematic view, in vertical section, of a porous surface layer of the element of the invention before forming, including electrodes, showing the metal particles dispersed in, and supported by, the layer and electrical connections among the particles.

FIG. 12 is a schematic view, in vertical section, of an insular mass of silver particles in one surface layer of an element according to the invention. The element consisted of a porous dielectric material having micropores and carrying ultrafine metal particles dispersed in, and supported by, the porous surface layers on both sides, with joints for electrodes formed by sputtering at four points on the thin film of the supported metal particles on each of the two sides of the dielectric, silver wires coiled separately round the individual points and the dielectric portions together, and four electrodes 1, 2, 3, and 4 secured with silver paste to the silver wires at four points on one side for the determination of the voltage-current characteristics by the four-terminal method. In this state the porous surface layers of the element are relatively uniform in structure and the entire element responds in the manner as shown in FIG. 10.

Figure 13:
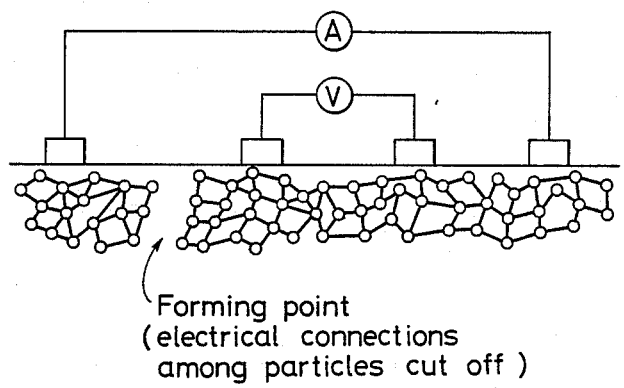
FIG. 13 is a schematic view, in vertical section, of a porous surface layer of the element of the invention after forming, includings electrodes, showing the metal particles dispersed in, and supported by, the layer and electrical connections and disconnections among the particles.
Figure 14:
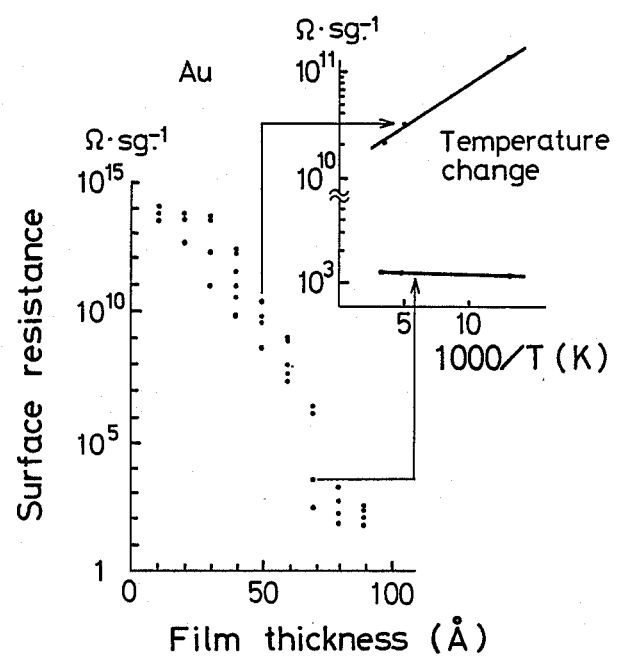
FIG. 14 is a graph showing the relations between the surface resistance of a vacuum-deposited film of gold having a mass film thickness of 10 to 100 Å and the film thickness and between the surface resistance and the temperature when the film thickness is kept constant.

FIG. 13 is a schematic view, in vertical section, of the same part as shown in FIG. 12, after the application of a high voltage to the element in the state of FIG. 12. In the part shown, electrical connections between silver particles are cut off locally in the portion where sintering resulted from heating to a high temperature by Joule heat. Resistance is higher there than in any other portion of the element, and the voltage applied to the element mostly concentrates on that portion. In this condition the element exhibits switching and memory functions as illustrated in FIG. 11.

The mechanism that dictates such functions is not clearly known yet. It is presumed, however, that tunnel electron conduction is promoted by a chemical action induced, in turn, between oxygen and the surface of silica glass as an insulator in a high electric field. The distance between silver particle masses severed in the sintered portion is approximately 100 Å, and if a voltage of 15V is applied there, an electric field as large as $15/100 \times 10^{-8} = 1.5 \times 10^7$ V/cm results.

Next, the process of the invention for producing a composite material will be described.

The process according to the invention is characterized by forming a thin film of conductive ultrafine metal particles on at least the porous surface layers of a porous dielectric and dispersing the thin film metal, in a size similar to the pore opening, continuously or partly continuously in the porous layers, whereby a three-dimensional composite material is obtained. The thin film of metal particles is formed by either of two means, the wet and dry methods.

The film forming by the wet method will now be explained.

One or two solutions are prepared which are chosen from among aqueous solutions of at least one of organic and inorganic salts of a metal to be formed into a film and organic solvent solutions of at least one of organic and inorganic salts of the metal.

A porous dielectric substance provided beforehand is immersed into the above solution or mixed solution. This is more advantageously performed by placing the porous dielectric under reduced pressure prior to the immersion and then immersing it into the bath. If the dielectric having micropores is directly placed into the bath, the solution finding its way from the surface into the dielectric seals up air inside the pores, building up the pressure of the contained air bubbles or residual gas to such a degree that it can crack the dielectric.

The immersed dielectric is then taken out of the bath and dried. The drying is intended to enable the dielectric to carry a desired amount of metal salt rapidly within the substrate and permit the subsequent step of reducing the metal salt with a metal to be concluded within a short period of time. Owing to the solubility of the particular solution or other limitation, the dielectric is sometimes unable to support a necessary amount of the metal salt by a single sequence of impregnation and reduction. In such a case, the cycle of immersion and drying may be repeated the number of times required for the porous layers of the dielectric to pick up the predetermined amount of the metal salt. The immersed and dried porous dielectric is placed in a reducing solution or reducing gas atmosphere to reduce the metal salt adsorbed by or deposited in the porous layers to the metal.

While the drying prior to reduction is not always required, it is preferred because the reaction for reduction of the metal salt in a dissolved state will need a somewhat longer period due to the diffusion resistance in the liquid phase.

In the manner described above, a gas-sensitive composite material of the invention comprising a porous dielectric having micropores and a thin film of ultrafine metal particles dispersed in, and supported by, at least the porous surface layers of the dielectric is obtained.

Next, manufacture by the dry method will be explained.

The process of the invention may employ the conventional techniques for forming two-dimensional discontinuous films, such as sputtering, vacuum deposition, and chemical vapor deposition (CVD). Conventionally, a smooth, flat sheet, for example, of silica or alumina, is used as a substrate and a metal film is formed thereon by sputtering, vacuum deposition, or CVD. According to the invention, by contrast, a composite material is formed which has a thin film of ultrafine metal particles dispersed in, and supported by, at least the porous surface layers of a porous dielectric having micropores.

Sputtering or vacuum deposition forces the metal molecules or atoms straightly forward under vacuum. Consequently, the metal particles do not reach the full depth of a porous body but are supported only in a thin layer of a thickness equal to the pore opening or at most several pore openings of the porous surface layer. With the composite material of the invention it is only necessary that the porous dielectric have porous surface layers.

When CVD is resorted to, the depth to which the ultrafine metal particles are supported by the porous portion of a dielectric depends on the ratio of the CVD reaction rate to the diffusion rate of molecules in the porous portion. If the diffusion takes place faster than the reaction the molecules spread throughout the porous portion and are supported by the entire portion. Conversely if the diffusion fails to catch up with the reaction, the molecules are supported by only the surface portions. In either case the end of the invention is attained.

As has been described hereinbefore, the composite material of the invention comprising a metal and a dielectric is electrically sensitive to various gases. It combines switching and memory actions, both of which are new functions not possessed by existing gas sensors. Moreover, these functions are stable. With these features the composite material of the invention is not merely suited for the uses of conventional gas sensors but also expected to find many other applications. Its electrical applications include biomedical instruments such as high-sensitivity strain gages, displacement transducers, temperature sensors, IR detectors, nonlinear detectors, electronic or optical emitters, and high-resolution vidicons. Among potential non-electronic applications are the use of insular permalloy films that attain enhanced hysteresis effects, utilization of the light absorptivity of the films in solar heat collectors, and even as means for producing positronium.

While certain presently preferred embodiments of the present invention have been described using silica glass as the dielectric and silver as the metal in the form of ultrafine particles, it is not intended to limit the invention to such embodiments, but various modification may be made therein without departing from the spirit and scope of the invention as set forth in the following claims.

I claim:

1. A gas-sensitive composite material comprising a porous dielectric having micropores and a thin film consisting of ultrafine metal particles dispersed in, and supported by, at least the porous surface layers of the dielectric.

2. A composite material according to claim 1 wherein said porous dielectric is one consisting of a substance selected from the group consisting of porous glass, porous alumina, porous titania, and porous zirconia.

3. A composite material according to claim 1 wherein said thin film consisting of ultrafine metal particles is one consisting of ultrafine particles of at least one metal selected from the metals of Groups IB, IIB, VIIB, and VIII.

4. A composite material according to claim 3 wherein said thin film of ultrafine metal particles is one consisting of ultrafine particles of at least one metal selected from Ag, Au, Cu, Fe, Co, Ni, Ru, Rh, Pd, Pt, Ir, Cr, Al, Zn, Sn, In, and Pb.

5. A composite material according to claim 1 wherein said porous surface layers of said porous dielectric have a thickness of 50 to $10^7$ Å.

6. A composite material according to claim 1 wherein the total volume of micropores 500 Å or smaller in size that are present in the porous surface layers of said porous dielectric account for 10 to 70% of the total volume of at least said porous surface layers.

7. A composite material according to claim 1 wherein the gases to which said material is sensitive are $O_2$, NO, $N_2O$, $NO_2$, $SO_2$, $SO_3$, CO, $H_2$, $NH_3$, methane, ethylene, ethane, propylene, and propane.

* * * * *

UNITED STATES PATENT AND TRADEMARK OFFICE
CERTIFICATE OF CORRECTION

PATENT NO. : 4,774,129

DATED : September 27, 1988

INVENTOR(S) : Hiroshi Komiyama

It is certified that error appears in the above-identified patent and that said Letters Patent is hereby corrected as shown below:

On the Title Page, Item [73], delete "Toa Nenryo Kogyo K.K., Tokyo, Japan" and insert --. Hiroshi Komiyama, Tokyo, Japan; Toa Nenryo Kogyo K.K., Tokyo, Japan--.

Signed and Sealed this

Eighteenth Day of April, 1989

Attest:

DONALD J. QUIGG

*Attesting Officer*  *Commissioner of Patents and Trademarks*